(12) United States Patent
Ng

(10) Patent No.: US 11,331,486 B1
(45) Date of Patent: May 17, 2022

(54) METHOD FOR REVERSING HEARING LOSS

(71) Applicant: Milly Ng, Hong Kong (HK)

(72) Inventor: Milly Ng, Hong Kong (HK)

( * ) Notice: Subject to any disclaimer, the term of this patent is extended or adjusted under 35 U.S.C. 154(b) by 350 days.

(21) Appl. No.: 16/529,389

(22) Filed: Aug. 1, 2019

(51) Int. Cl.
*A61N 1/36* (2006.01)
*A61N 1/05* (2006.01)
*A61B 5/12* (2006.01)

(52) U.S. Cl.
CPC ....... *A61N 1/36036* (2017.08); *A61N 1/0541* (2013.01); *A61B 5/121* (2013.01)

(58) Field of Classification Search
CPC ... A61N 1/36036; A61N 1/0541; A61B 5/121
See application file for complete search history.

(56) References Cited

U.S. PATENT DOCUMENTS

| | | | | |
|---|---|---|---|---|
| 3,563,246 | A * | 2/1971 | Puharich | A61N 1/32 607/55 |
| 5,800,458 | A * | 9/1998 | Wingrove | A61N 1/3603 607/2 |
| 2008/0287859 | A1 * | 11/2008 | Miller | A61B 17/3472 604/21 |
| 2014/0194774 | A1 * | 7/2014 | Gilligan | A61B 5/0022 600/559 |
| 2016/0361539 | A1 * | 12/2016 | Nathanson | A61N 1/0452 |

* cited by examiner

*Primary Examiner* — Gary Jackson
*Assistant Examiner* — Sebastian X Lukjan
(74) *Attorney, Agent, or Firm* — Leavitt Eldredge Law Firm

(57) ABSTRACT

A method of reversing hearing loss using a therapy stimulator machine that includes a first and second handheld probe electrode; using the hand held probe electrodes with water to apply pressure to locations and at the same time wiggle the probe electrodes around the patient's ear to stimulate hearing loss reversal. Simultaneously an isolated sound source is applied to the side of the ear under treatment so patient would be able to appreciate the improvement in the hearing capability instantly.

9 Claims, 4 Drawing Sheets

METHOD FOR REVERSING HEARING LOSS

BACKGROUND

1. Field of the Invention

The present invention relates generally to methods to reverse hearing loss, and more specifically, to a method that utilizes electrostimulation to aid in reversing hearing loss.

2. Description of Related Art

Methods to aid in reversing hearing loss are common in the art. There are hearing aid devices that can be worn, as well as invasive and dangerous treatments. These methods either require the patient to use an aid or come with complications associated with the treatment. Accordingly, it is an object of the present invention to provide a method to aid in reversing hearing loss using electrostimulation, which is relatively painless, effective, and long lasting.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
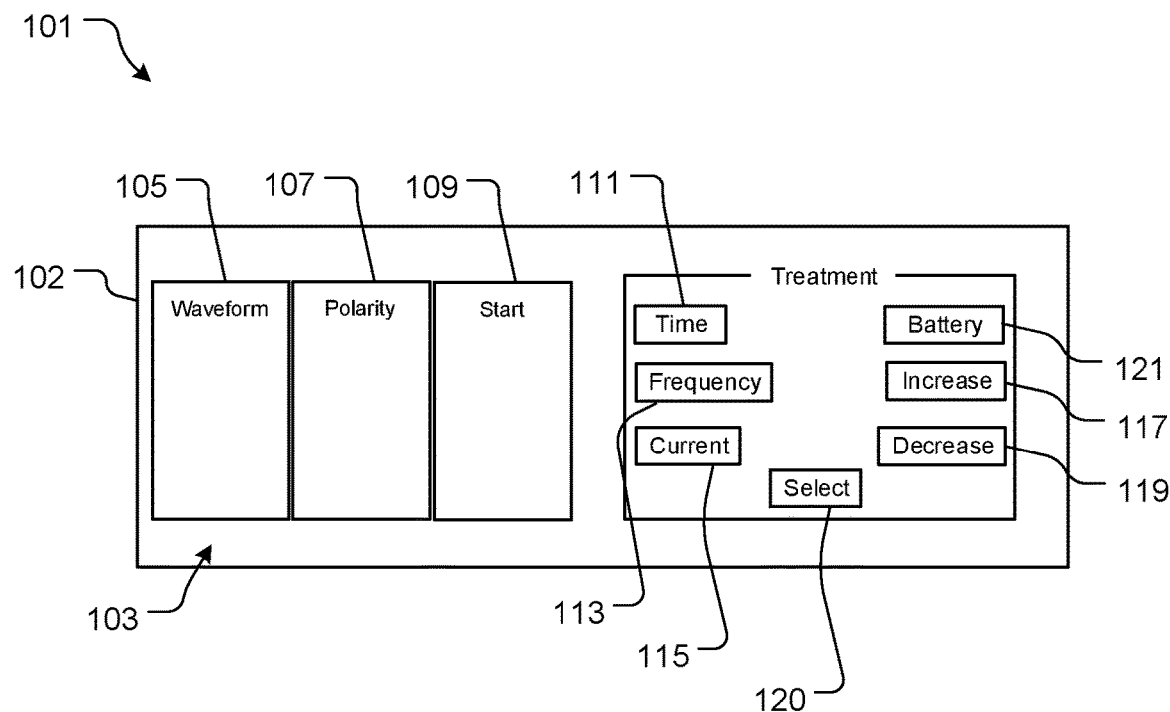
FIG. 1 is a front view of a therapy stimulator machine in accordance with the present invention.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional methods of reversing hearing loss. Specifically, the present invention provides for a minimal pain and recovery period procedure that is effective in aiding in reversing hearing loss for a lasting period. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
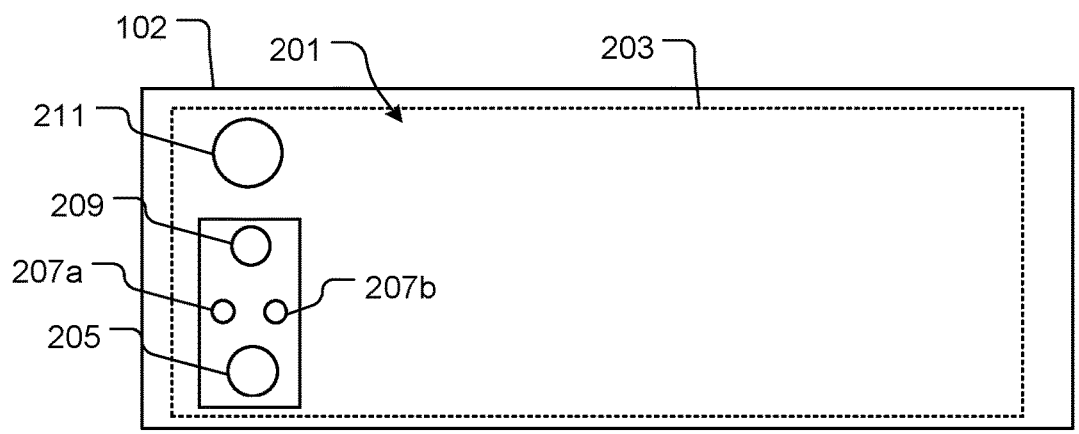
FIG. 2 is a back view of the machine of FIG. 1.

Referring now to the drawings wherein like reference characters identify corresponding or similar elements throughout the several views, FIGS. 1-2 depicts front and back views of a therapy stimulator machine 101 for use in accordance with the present invention.

In the present invention, the machine 101 is used during a method and procedure, as will be discussed herein. It should be appreciated that the machine can vary, however, the machine discussed is the preferred embodiment.

The machine 101 includes a housing 102 with a front panel 103 that can include a plurality of controls that allow for the user to set the machine to desired settings. As shown, the settings can include a waveform selection 105, a polarity selection 107, and a start/activation button 109. In addition, the user can select needed treatment elements, such as a treatment time 111, a desired frequency 113, and a current selection 115. The user will utilize the controls including increase 117, decrease 119, and select 120 to set the treatment. For example, the user can select a treatment time of 20 minutes, at a frequency of 0.3 Hz. Upon activation of the start button, the treatment will start at the desired frequency for the desired time.

As shown, the panel can further include a battery indicator 121 to indicate a level of battery charge. In the preferred embodiment, the battery 203 is a rechargeable battery.

As shown in FIG. 2, the housing 102 can further include a back panel 201, wherein the back panel includes a plurality of ports and other elements. As shown, such elements can include a jack 205 for connecting the hand held probe electrodes, a jack 207*a-b* for using adhesive pads, a knob 209 for adjusting audio volume, and a speaker 211, wherein the speaker can indicate that the time is up or the like.

Figure 3:
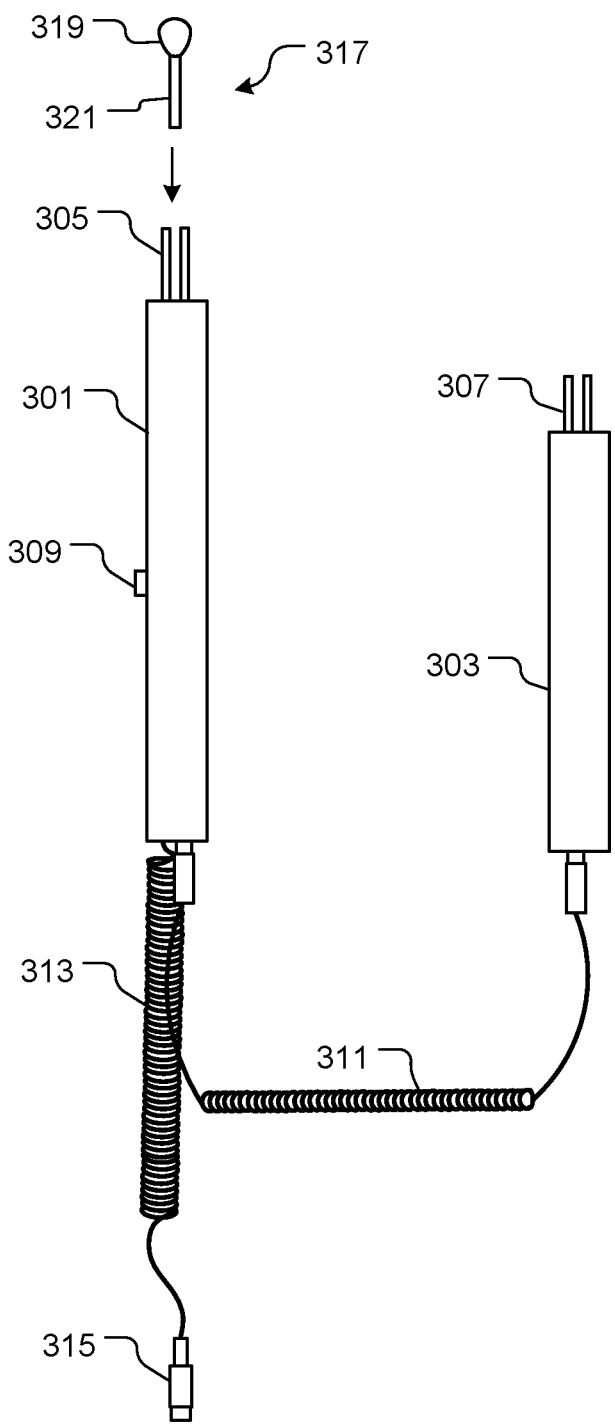
FIG. 3 is a top view of a first and second hand held probe electrode in accordance with the present invention.

In FIG. 3, a first and second hand held probe electrodes 301, 303 are shown. It should be appreciated that in the preferred embodiment, the electrodes 301, 303 include dual Q probe electrodes 305, 307 composed of stainless steel, and the first electrode 301 can include an on/off button 309 configured to activate and deactivate the electrodes. The first and second electrodes 301, 303 are electrically connected via a coiled wire banana plug 311 and a thicker extensible coiled wire 313 is connected to the first electrode 301 and includes a connector 315 for engaging with the jack 205 of the housing. It should be appreciated that the probe electrodes connect to the housing for power and activation of electro stimulation.

In the preferred embodiment, a cotton swab 317 is cut in half and wet with water, such that the cotton bud 319 is saturated. The shaft 321 of the cotton swab 317 can then be inserted into the electrodes 305 such that the water is in communication with the metal, thereby allowing for conductivity.

It should be appreciated that one of the unique features believed characteristic of the present application is the use of machine 101 in connection with the first and second probe electrodes to provide pressure to a plurality of locations associated with a patient's ear in order to aid in reversing hearing loss for the patient.

Figure 4:
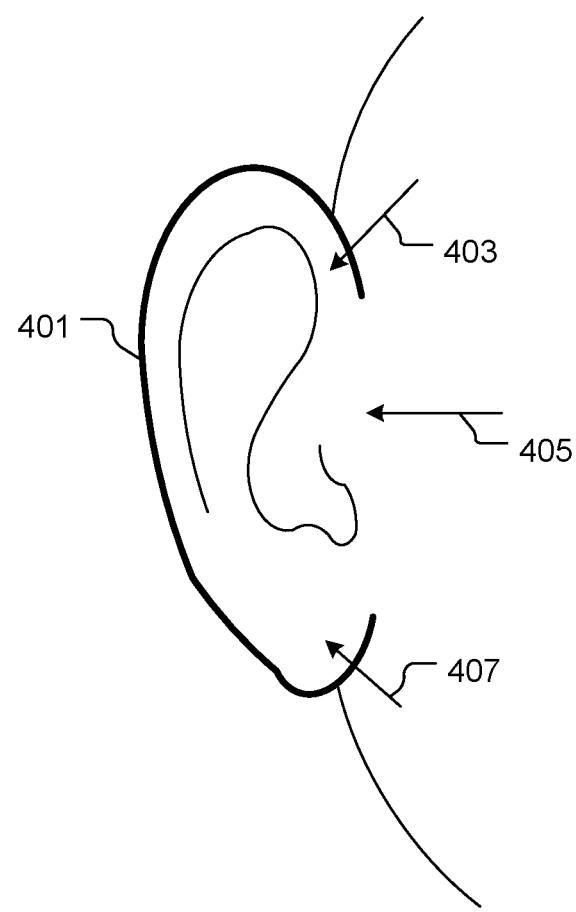
FIG. 4 is a front view of a patient's ear with treatment locations in accordance with the present invention.

In FIG. 4, a diagram depicts three treatment locations associated with the patient's ear 401. The first location 403 is at the upper point of the ear connecting to the face. The professional will bring the two cotton buds to the location and apply pressure such that the two cotton buds touch each other and start to wiggle gently. Not too hard that might hurt the patient. It should be appreciated that this point is rather delicate so gentle pressure should be applied. The patient is advised to voice out if they start to have needle feeling. Usually the needle feeling will accompany with hearing improvement. If after wiggle for about 5 moves, patient still hasn't felt the needle feeling, practitioner should shift half mm to search for a better point. Feeling needle means effective. Not feeling needle means the point is useless. Wiggle for about 10 moves (or less according to the tolerance of the patient. Avoid overdo) then go to the 2nd point.

The second point 405 is located at the middle of the ear. One electrode is placed at the front and the other at the back so giving a through and through effect. Both electrodes are wiggled at the same time. This point is the most intense of the 3. Quite often patients are seen with face turn red as feeling intense needle and this is also the most effective of the 3 points.

The third point 407 is located at the lowest point of the ear in connection to the face. The practitioner proceeds to place the electrodes thereon and wiggle and search for the needle feeling.

Figure 5:
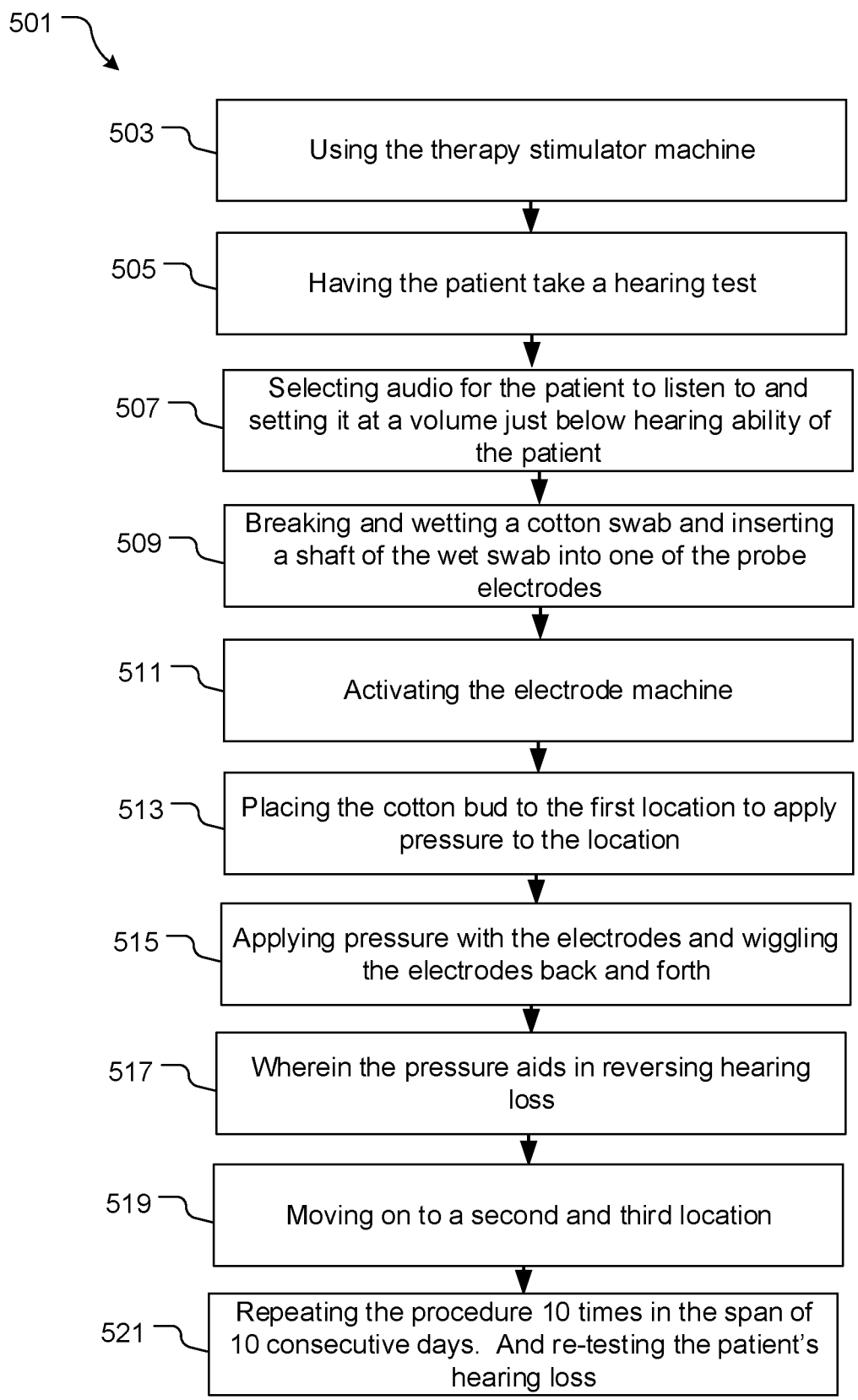
FIG. 5 is a flowchart of the method of use associated with reversing hearing loss in accordance with the present invention.

In FIG. 5, a flowchart 501 depicts a method of reversing hearing loss. During use, the therapy stimulator machine with the first and second hand held probe electrodes is used, as shown with box 503. It is advised that a patient take a hearing test by an audiologist prior to starting treatment, thereby having a base point to compare to at the end of treatment, as shown with box 505. The patient should select an audio content, such as a song, wherein the audio content is approximately 10 minutes long, and the audio content is played to the patient during treatment, thereby allowing for the patient to provide feedback as to the effectiveness of the treatment, as shown with box 507. It should be appreciated that to isolate the sound source, the patient is asked to put on the headset for the side of the ear that is under treatment and turn the volume of the song to a level that the patient just cannot hear. During treatment, if the patient begins to hear the song, this means that there is an improvement. The physician and/or patient may make a record of levels of hearing to monitor improvement, thereby being encouraging to the patient.

A cotton swab is broken in half and wet, such that the cotton bud is wet, and the shaft is inserted into the first hand held probe electrode, thereby putting water in electrical communication with the probes, as shown with box 509. The user will activate the machine, either through use of the button on the probe or through the activation button on the housing, as shown with box 511. The cotton bud is then placed on the first location, such that pressure is applied to the first location, as shown with box 513. The user will apply pressure and wiggle the electrodes back and forth, and then move onto the next location, as shown with box 515. It should be appreciated that the pressure is created through electrostimulation, preferably at a frequency of 0.3 Hz, wherein the pressure reverses hearing loss, as shown with box 517. The user can then move on to the second and third locations, as shown with box 519. During a single session, the treatment is repeated two times at all three points, with each round running 30-45 minutes and having short rests in between. It should be appreciated that in the preferred embodiment, the procedure is repeated for 10 days on a consecutive daily basis for best results, wherein the patient is advised to take a second hearing test after the treatment, as shown with box 521.

It should further be appreciated that the patient should sign an agreement that they acknowledge the continuity of the treatment and the sensation during the treatment. The patient must complete all 10 consecutive days of the procedure and comply with the rules of drinking 2-3 liters of water, refraining from caffeine, alcohol, and smoking.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method of reversing hearing loss, comprising:
   providing a therapy stimulator machine having:
   a housing having a front panel and a back panel, the housing having a rechargeable battery inside, the housing having a start button;
   a first hand held probe electrode connected to a second hand held probe electrode via a banana plug, the first hand held probe electrode having an on/off switch, the first hand held probe is configured to removably engage with a cotton swab;
   a cord attached to the first hand held probe electrode and plugged into the housing;
   a frequency selection button configured to allow a user to select a desired frequency;
   advising a patient to have a hearing test done by an Audiologist;
   selecting an audio content to be played to the patient during treatment;
   setting a volume of the audio content to a level just below a patient's hearing ability;
   breaking the cotton swab such that the cotton swab has a shaft and a cotton bud;

wetting the cotton bud of the cotton swab;
inserting the shaft of the cotton swab into the first hand held probe electrode such that water will come into contact with metal of the first hand held probe electrode;
activating the electrode machine through the start button;
placing the cotton bud to a first location along a patient's ear; and
applying pressure to the first location through the cotton bud, the pressure created through electrostimulation created by the therapy stimulator machine;
wherein the application of pressure to the first location stimulates hearing restoration through evidence of the patient starting to hear the audio content at a level which before treatment the patient could not hear.

2. The method of claim 1, wherein the desired frequency is 0.3 Hz.

3. The method of claim 1, wherein the therapy stimulator machine further includes:
a waveform selection;
a polarity selection;
a time selection;
a current selection; and
a battery indicator.

4. The method of claim 1, further comprising:
repeating the treatment daily for ten days.

5. The method of claim 1, further comprising:
advising the patient to take a second hearing test.

6. The method of claim 1, further comprising:
moving the cotton bud to a second location associated with the patient's ear; and
applying pressure to the second location, the application of pressure stimulating hearing restoration.

7. The method of claim 6, further comprising:
moving the cotton bud to a third location associated with the patient's ear; and
applying pressure to the third location, the application of pressure stimulating hearing restoration.

8. The method of claim 7, further comprising:
repeating treatment at the first location, second location, and third location two more times during a continuous treatment session.

9. The method of claim 1, further comprising:
applying pressure to the first location with the first hand held probe electrode and the second hand held probe electrode; and
wiggling the first hand held probe electrode and the second hand held probe electrode back and forth.

* * * * *